United States Patent [19]

McConnell

[11] Patent Number: 4,813,419
[45] Date of Patent: Mar. 21, 1989

[54] METHOD AND APPARATUS FOR COMMUNICATING INFORMATION REPRESENTATIVE OF SOUND WAVES TO THE DEAF

[76] Inventor: Jeffrey D. McConnell, 3504 W. Sixth, Spokane, Wash. 99204

[21] Appl. No.: 172,945

[22] Filed: Mar. 22, 1988

Related U.S. Application Data

[63] Continuation of Ser. No. 835,962, Mar. 4, 1986, abandoned, which is a continuation-in-part of Ser. No. 669,240, Nov. 7, 1984, abandoned.

[51] Int. Cl.$^4$ .............................................. A01N 1/36
[52] U.S. Cl. ................................... 128/421; 128/1 R; 128/421
[58] Field of Search ............ 128/1 R, 421, 427, 420.5, 128/420.6, 1 B; 381/68, 68.3; 340/470

[56] References Cited

U.S. PATENT DOCUMENTS

| | | | |
|---|---|---|---|
| 1,652,283 | 1/1928 | Morton . | |
| 2,150,364 | 3/1939 | Dudley | 179/107 |
| 2,233,848 | 3/1941 | Polk | 179/107 |
| 2,582,277 | 1/1952 | Powlison | 343/225 |
| 3,509,289 | 4/1970 | Briskey et al. | 179/107 R |
| 3,766,331 | 10/1973 | Zink | 179/107 R |
| 3,954,101 | 5/1976 | Wachspress | 179/107 R |
| 4,139,742 | 2/1979 | Walker | 179/107 |
| 4,167,189 | 9/1979 | Tachi et al. | 128/421 |
| 4,237,448 | 12/1980 | Zibell | 179/107 FD |
| 4,340,063 | 7/1982 | Maurer | 128/421 |
| 4,515,158 | 5/1985 | Patrick et al. | 179/107 R |
| 4,581,491 | 4/1986 | Boothroyd | 128/420.5 |

FOREIGN PATENT DOCUMENTS 3003315 8/1981 Fed. Rep. of Germany ... 128/420.5

OTHER PUBLICATIONS

Carol Lee DeFilippo, "Laboratory Projects in Tactile Aids to Lipreading," *Ear and Hearing* 5(4), 1984.
Harriet Kaplan, "A Vibrotactile Fitting for a Totally Deaf Adult," *The Hearing Journal*, Feb. 1983.
Siemens Announcement and Technical Data Sheet for Mini-Fonator Wearable Vibrotactile Aid.
C. M. Reed, W. M. Rabinowitz, N. I. Durlach, L. D. Braida, S. Conway-Fithian and M. C. Schultz, "Research on the Tadoma Method of Speech Communication," *J. Acoust. Soc. Am.* 77(1), Jan. 1985.
Moise H. Goldstein, Jr. and Adele Proctor, "Tactile Aids for Profoundly Deaf Children," *J. Accoust. Soc. Am.* 77(1), Jan. 1985.
David Franklin, "Tactile Aids, New Help for the Profoundly Deaf," *The Hearing Journal*, Feb. 1984.
Ronald T. Verrillo, "Psychophysics of Vibrotactile Stimulation," *J. Acoust. Soc. Am. 77(1), Jan. 1985.*
Frank A. Geldard, "The Mutability of Time and Space on Skin," *J. Acoust. Soc. Am.* 77(1), Jan. 1985.
James C. Craig, "Tactile Pattern Perception and its Perturbations," *J. Acoust. Soc. Am.* 77(1), Jan. 1985.
Grace H. Yeni-Komshian and Moise H. Goldstein, Jr., "Identification of Speech Sounds Displayed on a Vibrotactile Vocorder," *J. Acoust. Soc. Am.* 62(1), Jul. 1977.

(List continued on next page.)

*Primary Examiner*—Edward M. Coven
*Attorney, Agent, or Firm*—Jackson & Jones

[57] ABSTRACT

A method and apparatus of communicating audio signals to the deaf is described. In accordance with the method described, electrical impulses characteristic of sound waves are applied either directly to the tactile sensory nerves by means of an implant or are applied simultaneously with vibrations representative of the sound waves to the nerve endings located at the skin surface. In accordance with the apparatus, a nerve stimulator applies a voltage representative of the sound waves across a pair of implanted electrodes in contact with the tactile sensory nerve such as the radial nerve branch located in the wrist or applies vibrations representative of the sound waves by means of a transducer to the skin, e.g. the finger tips of the deaf person, and electrical impulses representative of the sound waves across a pair of spaced electrodes carried by the transducer so that the same nerve endings are stimulated with both the vibrations and the electrical impulses.

7 Claims, 4 Drawing Sheets

OTHER PUBLICATIONS

Carl E. Sherrick, "Touch as a Communicative Sense: Introduction," *J. Acoust. Soc. Am.* 77(1), Jan. 1985.
John R. Phillips and Kenneth O. Johnson, "Neural Mechanisms of Scanned and Stationary Touch," *J. Acoust. Soc. Am.* 77(1), Jan. 1985.
Carl E. Sherrick, "Basic and Applied Research on Tactile Aids for Deaf People: Progress and Prospects," *J. Acoust. Soc. Am.* 75(5), May 1984.
P. L. Brooks and B. J. Frost, "Evaluation of a Tactile Vocorder for Word Recognition," *J. Acoust. Soc. Am.* 74(1), Jan. 1978.
David W. Sparks, Patricia K. Kuhl, Alice E. Edmonds, and Gary P. Gray, "Investigating the MESA (Multipoint Electrotactile Speech Aid): the Transmission of Segmental Features of Speech," *J. Acoust. Soc. Am.* 63(1), Jan. 1978.

IMPLANT AREA

METHOD AND APPARATUS FOR COMMUNICATING INFORMATION REPRESENTATIVE OF SOUND WAVES TO THE DEAF

BACKGROUND OF THE INVENTION

1. Origin of the Invention

This invention is a continuation of the presently pending application Ser. No. 835,962, filed Mar. 4, 1986, abandoned, which in turn is a continuation-in-part of Ser. No. 669,240, filed on Nov. 7, 1984 abandoned and entitled METHOD AND APPARATUS FOR COMMUNICATING INFORMATION REPRESENTATIVE OF SOUND WAVES TO THE DEAF and assigned to the assignee of this application.

2. Field of the Invention

The present invention relates to a method and apparatus for communicating information representative of air pressure sound waves to deaf persons, and more particularly to a method and apparatus for translating sound waves into electrical signals and stimulating the tactile sensory nerves of the deaf person in accordance with such electrical signals.

3. Description of the Prior Art

The prior art's efforts at providing some measure of hearing for the totally and partially deaf has been directed primarily at stimulating the inner ear or cochlea with signals derived from sound waves. The stimulated cochlea would in theory transmit signals to the brain through the auditory nerve, which could be translated into information representing the original sound waves.

One example of such prior art efforts is described in an article entitled "Success for the 'Bionic Ear,'" appearing in the Mar. 12, 1984 issue of *Time Magazine*. According to this article, eight wires are implanted in the deaf person's inner ear and connected to an electrical plug extending through the skull. A microphone carried on the ear translates the sound waves into electrical signals which are then processed by a computer and applied to the implanted wires. Such prior art devices require delicate surgery, are expensive, and have not yet met with any great success.

Another prior art effort is described in U.S. Pat. No. 3,209,081 in which a hearing aid device in the form of a receiver implanted in the mastoid bone of the deaf person communicates with an external transmitter. The transmitter picks up sound waves through a microphone, translates the sound waves into audio signals, modulates a radio frequency (r.f.) signal with the audio signals and transmits the modulated r.f. signal to the implanted receiver. The receiver then demodulates the receiver signal and applies the demodulated signals to the skull of the patient, where they are hopefully transmitted through the bone to the patient's inner ear.

The reliability of such prior art methods and apparatus have not been adequately proven. Furthermore, the nature of the surgery required to implant devices into the skull has undoubtedly discouraged the widespread use of such apparatus.

Other prior art devices, commonly referred to as vibrotactile aids, impress vibrations against the deaf persons skin. U.S. Pat. Nos. 4,139,742 and 2,150,364 illustrate two such devices. The device disclosed in the '742 patent translates voice signals into mechanical vibrations, (having the same frequency patterns as the voice signals) and applies the vibrations to the nerve receptors adjacent the wrist area of the deaf or partially deaf person. The device disclosed in the '364 patent breaks up the voice signal into a plurality of frequency bands, rectifies the signal in each band and then passes the signal through a low pass filter (i.e. 0–20 Hz). The separate low frequency signals are converted to mechanical vibrations and impressed on the wrist and finger tips of the deaf persons. Such prior art devices have provided little, if any, help in enabling deaf people to understand or appreciate audio signals.

Researchers in the field have noted that the skin (or touch) sensory system is limited in its response to relatively low frequency tactile signals. For example Mr. David Franklin in an article entitled "Tactile Aid, New Help for the Profoundly Deaf" published in the February, 1984 issue of the Hearing Journal has suggested that the "[t]actile system is unable to feel frequencies that are much above 1000 HZ . . . " This phenomenon may account for the inability of the prior art tactile devices to stimulate the tactile nerve endings with signals characteristic of speech and music (i.e. above and below 1000 HZ). The higher frequency components (i.e. above 1000 Hz) inherent in audio signals such as speech and music are important in enabling the brain to corelate the received stimuli with sound.

Contemporary vibrotactile aids have employed both vibrators and electrodes spaced therefrom for applying stimulus representing various audio frequency bands to the sensory nerves located in the hand or wrist. See Carol Lee De Filippo' article entitled "Laboratory Projects in tactile aids to Lipreading" published in Volume 5 No. 4 (1984) of Ear & Hearing. Devices which apply electrical and vibratory stimulation to different areas of the skin have not gone beyond the research stage to my knowledge.

Although as described above the prior and contemporary art has suggested several techniques for enabling the deaf to hear, such techniques have not gained any widespread acceptance.

The method and apparatus of the present invention for communicating information representative of sound waves to the deaf overcomes the disadvantages of the above devices.

SUMMARY OF THE INVENTION

I have discovered that the tactile sensory nerves endings or corpuscles will respond to vibrations having frequencies characteristic of the sound waves inherent in normal speech (i.e. above and below 1000 Hz) when subjected to electrical impulses representative of such sound waves. While the response mechanism of the nerve endings or corpuscles is not completely understood it is believed that the electric field created by the electrical impulses decreases the regeneration time of the nerve endings or corpuscles and allows them to respond to the higher frequency vibrations thereby enabling the tactile sensory nerves and brain to corelate the received stimuli with sound waves. Where the tactile sensory nerves are directly accessible, e.g. by the use of an implant, electrical impulses characteristics of the sound waves may be used without vibratory signals to stimulate nerves and provide information representative of speech and other audio signals to the brain.

In accordance with the method of the present invention, sound waves are translated into electrical impulses having characteristics representative of the sound waves. The electrical impulses are (1) applied directly to the tactile sensory nerves originating in at least one hand of the deaf person by means of an implant (e.g. in the wrist area) having electrodes in contact with the nerves or (2) applied simultaneously with mechanical vibrations representative of the sound waves to the nerve endings or nerve corpuscles located for example in the finger tips.

The apparatus of the present invention includes a sound wave transducer, e.g., a microphone having an output circuit and arranged for generating electrical signals in the output circuit having characteristics representative of the incident sound waves. A nerve-stimulator has an input circuit connected to the output circuit of the sound wave transducer and includes at least one vibration transducer adapted to impart vibrations to the tactile sensory nerve endings located within an area of the skin (e.g. fingertips) of the person when pressed thereagainst and at least one pair of spaced electrodes adapted to contact the skin within said area for transmitting electrical impulses to the nerve endings. The vibrations and electrical impulses produced by the nerve stimulator are characteristic of the electrical signals in the output of the sound wave transducer, whereby the electrical impulses enhance the ability of the nerve endings to respond to vibrations having the higher frequency components contained in normal speech, e.g. above 1000 Hz.

Where the tactile sensory nerves are directly accessible, e.g. by means of an implant, the apparatus may include a pair of electrodes for applying electrical impulses characteristic of the sound waves directly to the nerves.

DESCRIPTION OF THE PREFERRED EMBODIMENT

The following specification taken in conjunction with the drawings sets forth the preferred embodiment of the present invention, although it should be understood that various modifications can be accomplished without departing from the spirit and scope of the invention.

Figure 1:
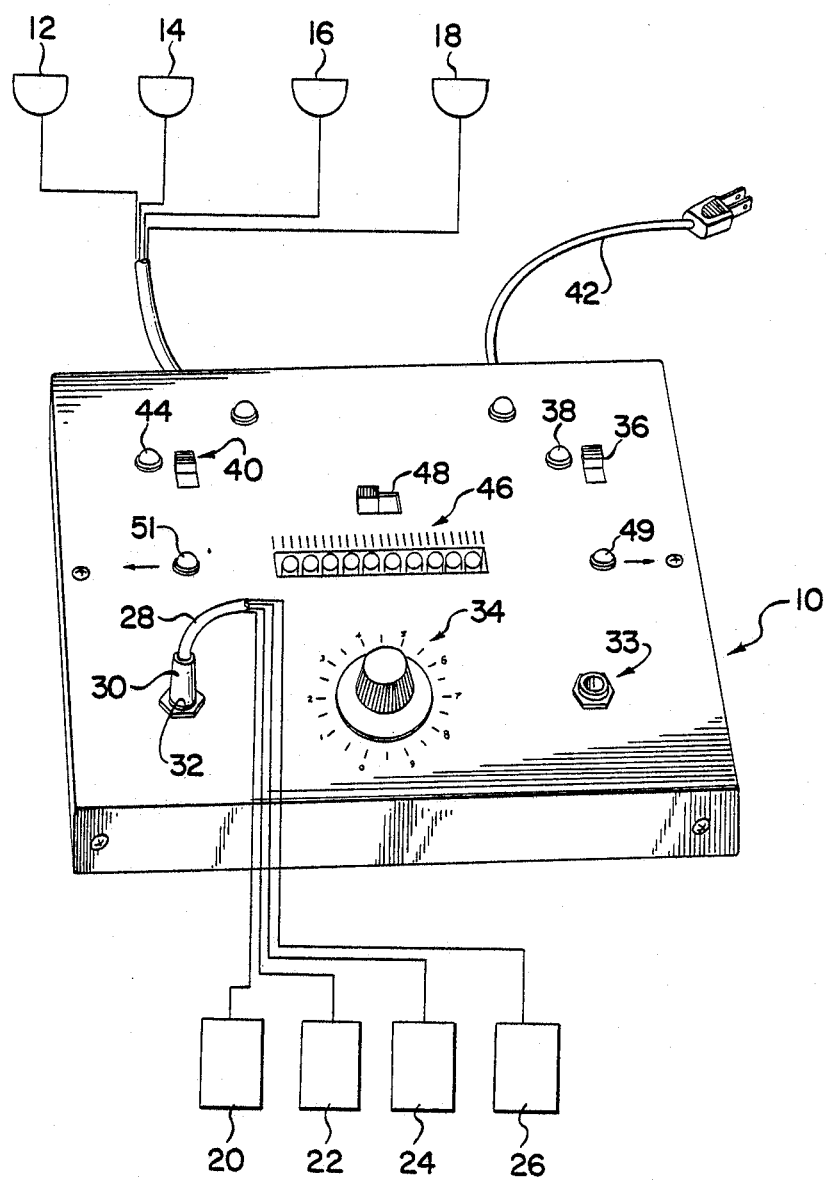
FIG. 1 is a perspective view of one preferred embodiment of the apparatus of the present invention.

Referring now to FIG. 1, a housing 10 encloses an audio-neural electrical circuit (shown in FIG. 3) for receiving electrical signals from sound wave transducers or microphones 12, 14, 16 and 18, and translating such signals into appropriate output signals which are applied to finger stimulators 20, 22, 24 and 26 via a four-wire cable 28.

Figure 5:
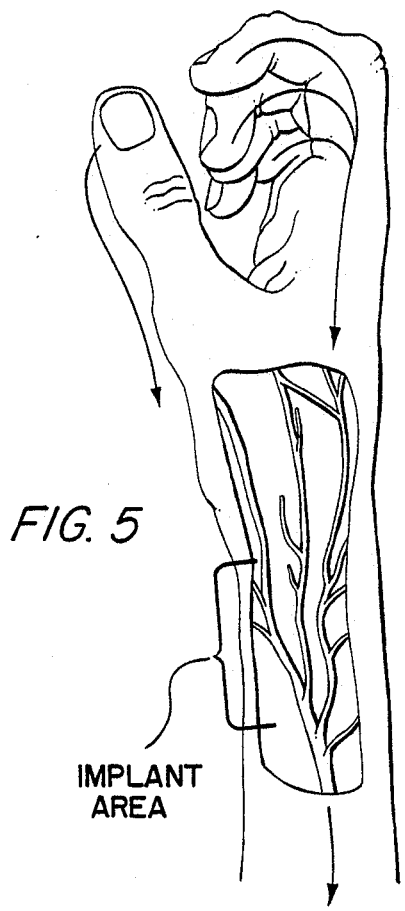
FIG. 5 is a partial cross-sectional view of a human wrist and hand illustrating the location of the radial nerve and the area for receiving the implant of FIG. 4.

As will be explained, the finger stimulators apply electrical impulses as well as vibrations characteristic of the sound waves to the deaf person's finger-tips. This stimulation is transmitted to the brain via the tactile sensory nerves such as the radial nerve, which is illustrated in FIG. 5. It is well known that the human brain can, under certain circumstances, compensate for missing sensory input. A case in point is Helen Keller, who became proficient with the use of her tactile sense in developing oral responses. By feeling the vibrations in a normal person's throat, she was able to reproduce similar vibrations. Through the use of her tactile sense, she learned to speak with more than adequate articulation. Through extensive experimentation, I have discovered that totally deaf persons, after suitable training, can translate the signals imparted to their fingertips by the stimulators 20–26 of my invention into meaningful auditory information. For example, spoken words, as well as other sounds such as music, can be understood and/or appreciated.

The cable 28 which applies the output signal from the audio-neural circuit to the finger stimulators 20–26 is coupled to the circuit by means of a jack 30 and connector 32. An auxiliary connector 33 is also provided for permitting audio signals from another source such as a tape, playback apparatus, etc., to be coupled to the circuit. A volume control knob 34 may be manually adjusted to provide an output signal of appropriate magnitude to the stimulators 20–26. A switch 36 is provided for connecting the circuit to a suitable source of power, i.e., a rechargeable battery. A pilot lamp or light-emitting diode 38 enables the operator to visually determine when the circuit is energized. Another switch 48 selectively connects the battery through a battery charger of conventional design to a source of a.c. power via cord 42. A light-emitting diode 44 visually informs the operator when the battery is being charged.

Figure 2:
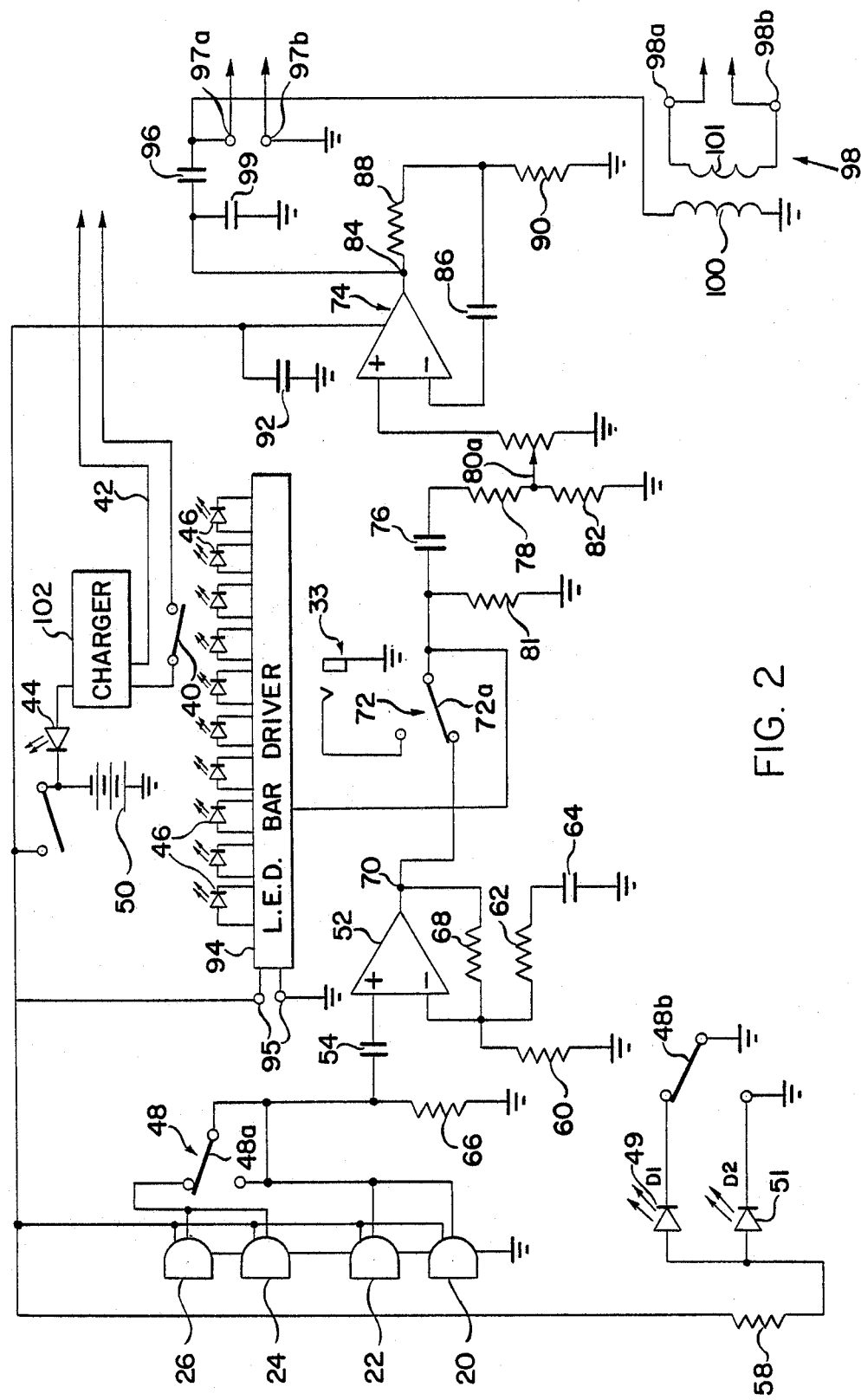
FIG. 2 is a schematic circuit diagram of one electrical circuit that may be employed in the apparatus of FIG. 1.

Ten light-emitting diodes collectively designated by numeral 46 provide a visual indication of the level of the output signal from the microphones 20–26, as will be discussed in connection with FIG. 2. The microphones 12 and 14 are always connected to the audio-neural circuit. A switch 48 enables the operator to also connect microphones 16 and 18 to the circuit, as is illustrated in FIG. 2. Light-emitting diodes 49, 50 are energized to indicate the use of only microphones 12 and 14 or all four microphones, respectively.

Referring now to FIG. 2, one terminal of the microphones 12–18 is connected to the positive terminal of a battery 50 and the other terminal is connected to the positive input of an operational amplifier 52 through a capacitor 54. As is illustrated, the microphones 16 and 18 are coupled to the amplifier 52 through the ganged switch 48. The switch 48 includes one contact 48a for connecting the microphones 16 and 18 to the input of the amplifier 52 and another contact 48b for connecting a light-emitting diode 49 between the positive terminal of the battery 50 and ground through a resistor 58, as illustrated. The diode 49 when energized indicates that microphones 16 and 18 are in the circuit. An additional light-emitting diode 51 is connected between the battery and ground through the resistor 58 to indicate that microphones 12 and 14 are also in the circuit. With the ganged switch 48 in the position illustrated, the microphones 12 and 14 are coupled to the input circuit of the amplifier 52 along with the microphones 16 and 18.

The operational amplifier 52 includes a negative input which is connected to ground through a resistor 60 in parallel with another resistor 62 and a capacitor 64, as shown. The junction of the capacitor 54 and the output of the microphones 12-18, is also connected to ground through a resistor 66. A feedback resistor 68 is connected between the output terminal 70 of the operational amplifier 52 and the negative input thereof.

A selector switch 72 selectively connects the output terminal 70 of the amplifier 52 or the auxiliary input jack 33 to the positive input of a second operational amplifier 74 through a coupling capacitor 76, a resistor 78 and a level control potentiometer 80. The wiper 80a of the potentiometer 80 is controlled by knob 34. A resistor 81 is connected between a movable contact 72a of the switch 72 and ground. Resistor 82 is connected between the wiper 80a and ground to form a voltage divider network with the resistor 78. The negative input of the operational amplifier 74 is connected to the output terminal 84 through a feedback capacitor 86 and a resistor 88. The junction of the capacitor 86 and resistor 88 is connected to ground through a resistor 90. A power input terminal of the amplifier 74 is connected to the positive terminal of the battery 50 and a filter capacitor 92 is connected between the positive terminal of he battery and ground.

A light-emitting diode bar driver 94 has an input coupled to the movable contact 72a of the switch 72 and output terminals connected to the ten light-emitting diodes 46. Power terminals 95 of the bar driver 94 are connected across the battery as shown. The bar driver 94 responds to the magnitude of the signal applied to the movable contact 72a of the switch 72 (i.e., the output from the amplifier 52 or the signal present on the auxiliary input jack 33) and energizes the diodes 46 serially as the magnitude is increased. Thus the number of the diodes 46 which are energized provide an indication of the magnitude or level of the sound picked up by the microphones 12-18 or the level of the auxiliary input signal, depending upon the position of the switch 72.

Figure 3:
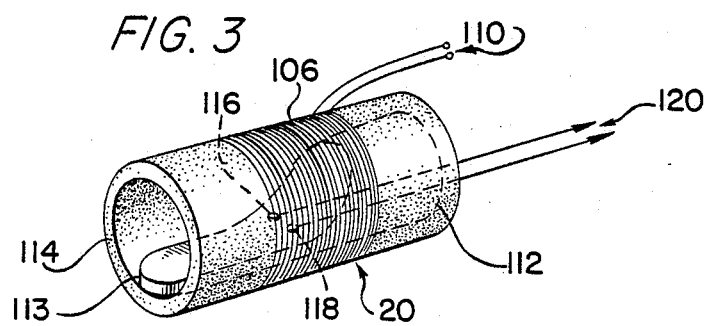
FIG. 3 is an enlarged perspective view, partially broken away, of one of the finger stimulators used in the apparatus of FIG. 1.

The output of the amplifier 74 is applied to one portion of the finger stimulators through a coupling capacitor 96 via terminals 97a and 97b and to another portion through transformer 98 via terminals 98a and 98b, as will become apparent in connection with the description of FIG. 3. The transformer 98 includes a primary winding 100 connected between ground and the terminal 97a and a secondary winding 101 connected across terminals 98a and 98b. Another filter capacitor 99 is connected between the output of the amplifier 74 and ground, as shown.

Each finger stimulator includes two input circuits, that is, for providing electrical impulses characteristic of the sound waves received by the microphones 12-18 and another for providing vibratory stimulations characteristic of the input to the microphones, as will become more apparent in reference to FIG. 3. The electrical impulses across the electrodes apparently modify the regeneration time the pacinian and meisner nerve corpuscles, thereby permitting finite discrimination of the stimuli at high and low audio frequencies. The circuit of FIG. 2 includes a conventional battery charger circuit 102 which is connected to a source of a.c. power (e.g., 120 volts, 60 Hz) through the cord 42 so that the battery can be periodically charged by operation of the switch 40. The light-emitting diode 44 connected in the output of the charger 102 is energized when the battery is being charged.

Referring now to FIG. 3, there is illustrated one of the finger stimulators 20-26. The stimulator includes a plastic tube 104 on which is wound a transducer winding 106 which is connected to the terminals 97a and 97b via input circuit 110 and cable 28. A magnetic metal core 112, preferably made of ceramic (or plastic) with magnetic particles blended into the ceramic, extends within the tube 104 and is separated from tube 104 by a foam sleeve 114. The magnetic core 112 includes a tongue 113 which is adapted to receive one finger of the operator. A pair of electrodes 116 and 118 insulated from the core are mounted on this tongue 116, as illustrated, so that the electrodes will contact the surface of the finger at spaced points when the finger is inserted into the stimulator. Electrodes 116, 118 are connected by a pair of wires (also insulated from the core) to an input circuit 120 which in turn is coupled to the output of the secondary winding 98b of the transformer 98 via cable 28.

In operation, the deaf person inserts a thumb and three fingers of one hand into the finger stimulators 20, 22, 24, 26. If desired, only three finger stimulators need be used for the thumb and two fingers. Power is then applied from the battery 50 to the circuit via switch 36 and the volume control knob 34 is turned until sufficient stimulation is received from the stimulators 20-26 to enable the deaf person to discriminate between various sound waves picked up by the microphones (or audio signals from a tape recorder or the like if the auxiliary input is being used).

With training many deaf persons are able to associate the stimulation received from the stimulators 20-26 with the various sounds responsible for the stimulation. Through the use of my invention, deaf persons have been able to understand spoken words, identify the speaker by the characteristics of his or her voice, and gain some appreciation for other sounds such as music, etc.

The following is a table of the component values used in the circuit of FIG. 2.

| Component | Value and/or Source |
| --- | --- |
| 52 | LM387-National Semiconductor Corp. |
| 50 | 12 volts |
| 54 | 470 f |
| 58 | 4.7K |
| 60 | 15K |
| 62 | 100 |
| 64 | 150 f |
| 66 | 680 |
| 68 | 100K |
| 74 | LM383-National Semiconductor Corp. |
| 76 | 470 f |
| 78 | 470K |
| 80 | 500K |
| 81 | 10 M |
| 82 | 330K |
| 86 | 470 f |
| 88 | 220 |
| 90 | 2.2K |
| 92, 99 | 0.2 f |
| 96 | 2200 f |
| 106 (FIG. 3) | approximately 130 turns of 30 gauge wire |

The component values provided in the above table are exemplary only.

Figure 4:
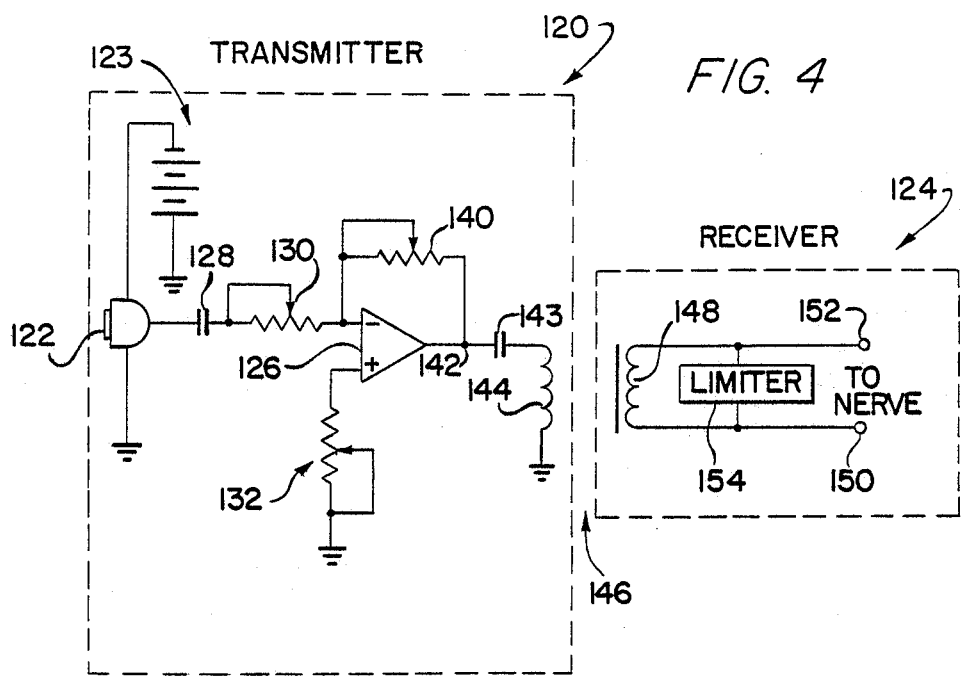
FIG. 4 is a schematic circuit diagram of a second preferred embodiment of the apparatus of the present invention in which an implant is employed to provide stimulation directly to the tactile sensory nerves.

Referring now to FIG. 4, there is illustrated an audio-neural communication system which may be worn by the user. The system includes a transmitter portion 120 which receives sound waves via microphone 122 and transmits electromagnetic waves characteristic of the sound waves to a receiver portion 124 implanted in the user's wrist area. The microphone 122 is connected between the positive terminal of a suitable battery 123 (e.g., 3.0 volts) and ground. The output of the microphone 122 is applied to the negative input of an operational amplifier 126 through a coupling capacitor 128 and a variable resistor 130. The positive input of the amplifier 126 is connected to ground through a level control potentiometer 132. An adjustable feedback resistor 140 is connected between the output 142 and the negtive input of the amplifier 126 to enable the gain of the amplifier to be adjusted. The output terminal 142 of the amplifier 126 is connected to a primary winding 144 of a transformer 146 through a capacitor 143.

The receiver implant or nerve stimulator 24 is encased in a suitable tissue-tolerant plastic material (not shown) and surgically implanted in the user's wrist area. The impant 124 includes a coil 148 which functions as the secondary of the transformer 144. The coil 148 converts the electromagnetic waves from the transmitter 120 into electrical impulses characteristic of the sound waves picked up by the microphone 122. The electrical impulses are applied across an output in the form of a pair of electrodes 150, 152 which are preferably inserted into one of the tactile sensory nerves originating in the hand. A voltage limiter 154 connected across the output electrodes serves to limit the voltage and/or current applied to the nerve to about 50–100 mv and 25–50 ma.

The radial nerve branch has been chosen as the most convenient of the tactile sensory nerves for receiving electrical impulses from the electrodes 152, 153. The radial nerve is of a sufficient bundle size and is accessible surgically. This nerve ascends the arm to the brachial plexus where it converges with the ulner the median nerves to enter the spine through the fourth to the seventh vertebrae. FIG. 5 generally illustrates the implant area and the portion of the radial nerve in that area. It should be noted that the ulnar or median nerves could be chosen to receive the electrodes. Each of these nerves traverse the wrist area.

The receiver implant 124 requires no battery and thus does not have to be removed once in place. In operation the user straps the transmitter 120 over his or her wrist so that the primary winding 144 of the transformer overlays the secondary winding 148. The resistors 130, 140 may then be adjusted to set the level of the input signal and the gain of the amplifier 126. The level control potentiometer 132 is readily accessible to the user to permit the magnitude of the stimulation received from the electrodes 152, 150 to be controlled with a given level of sound wave input. As with the less portable audio-neural communication system of FIGS. 1, 2 and 3, the system of FIG. 4 requires training before the user can associate the stimulation of the radial nerve with the sounds producing the stimulation.

Figure 6:
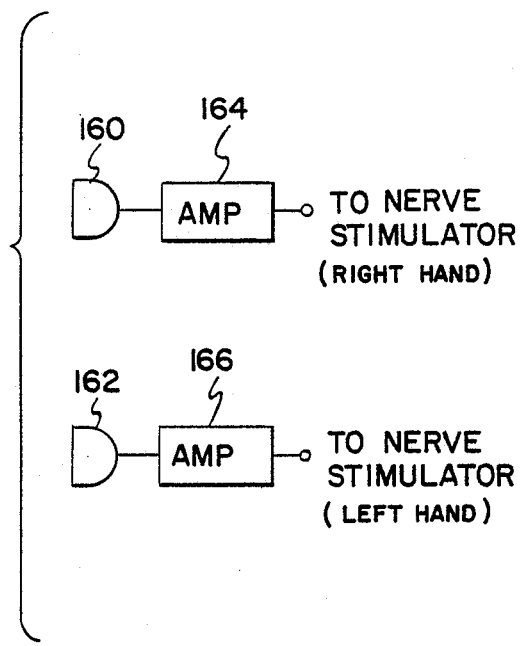
FIG. 6 is a block diagram of a circuit for providing stereo stimulation.

FIG. 6 illustrates a stereo system in which separate microphones 160, 162 are coupled to amplifiers 164, 166, respectively, with the output of such amplifiers applying output signals to the tactile sensory nerves of the right and left hands (or vice versa), respectively.

The amplifiers 164, 166 may each comprise the circuits shown in FIGS. 2 or 4 with the corresponding nerve stimulators.

Figure 7:
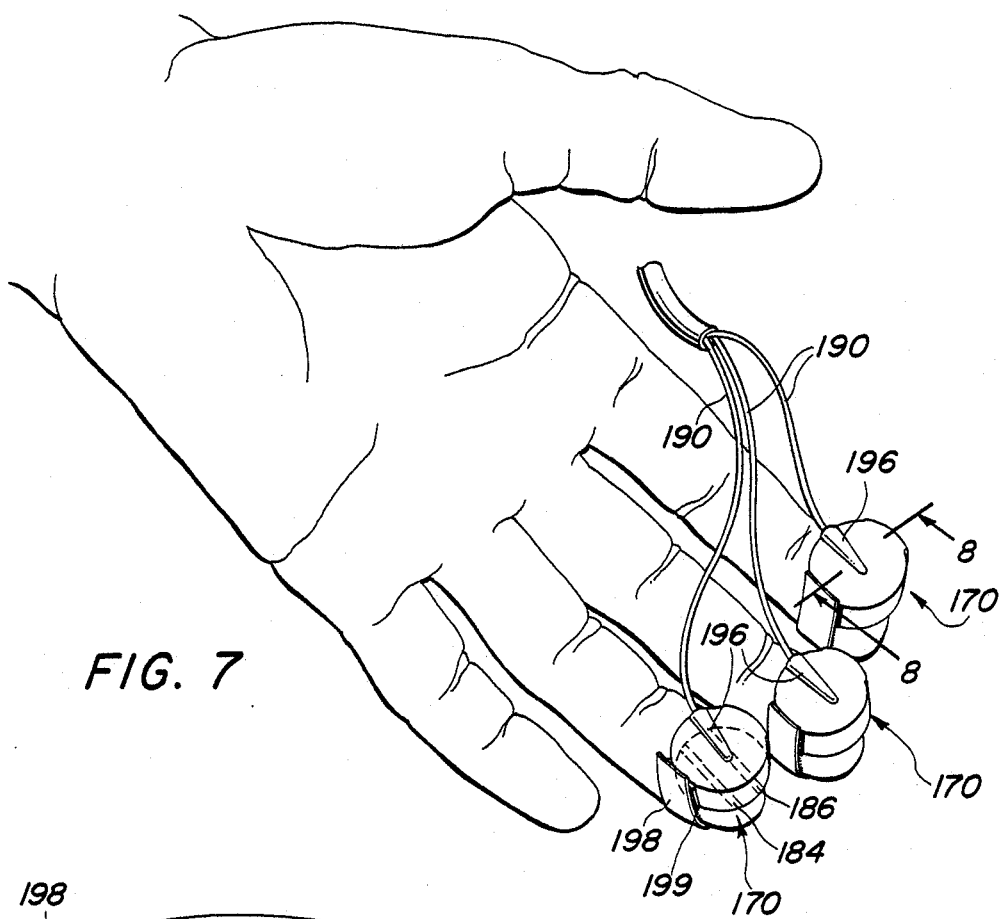
FIG. 7 is a perspective view of a hand with nerve stimulators applied to three fingers of the hand in accordance with another embodiment of the invention.
Figure 8:
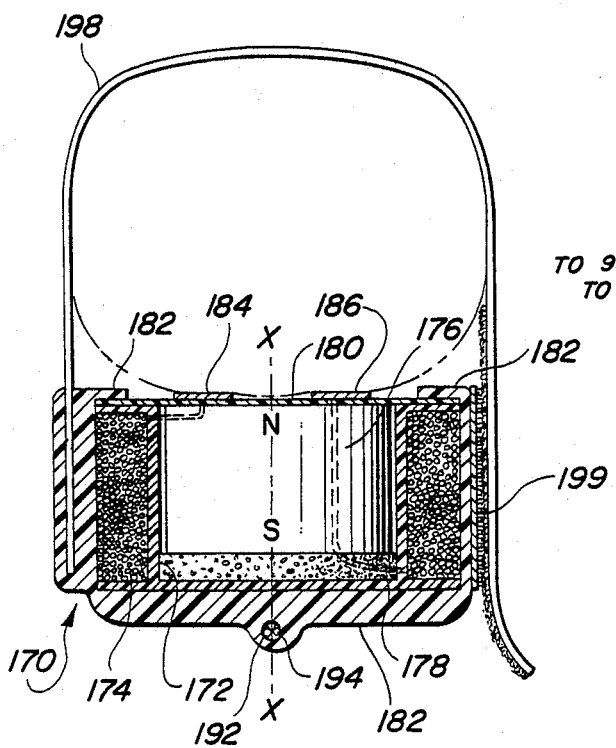
FIG. 8 is a cross-sectional view of one of the stimulators of FIG. 7 taken along line 8—8.
Figure 9:
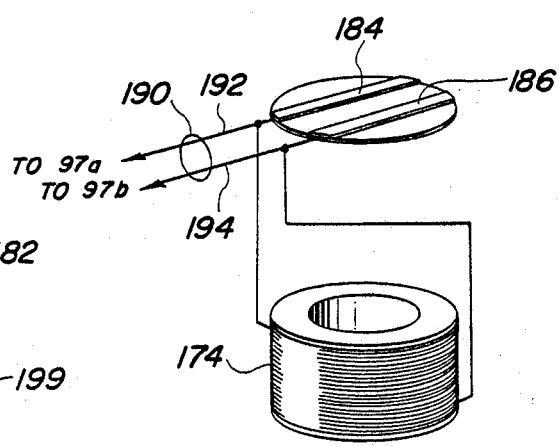
FIG. 9 is a schematic illustration of the vibration coil and electrodes included in the stimulator of FIG. 7.

Referring now to FIGS. 7, 8 and 9 there is illustrated another embodiment of the nerve stimulator for use in the present invention. Each nerve stimulator 170 comprises a hollow cylindrical core 172 made of a suitable insulating material such as a polyvinyl chloric plastic ("PVC"). A coil 174 is wound around the outside of the plastic core and a cylindrical permanent magnet 176 is disposed within the core so that an alternating current within the coil will cause the magnet to vibrate along the longitudinal axis X—X of the core. A compressible pad 178 in the form of a plastic sponge is located at one end of the magnet. A flexible sheet of insulating material 180 made for example of a suitable plastic such as PVC is secured over one end of the core 172 and coil 174 by an exterior platic coating 182 to retain the magnet 176 and compressible material 178 within the core 172.

A pair of elongated spaced electrodes 184 and 186 are connected to the top of the flexible sheet 180. A two wire cable 190 including wires 192 and 194 has its end embeded in the plastic coating 182 at 196. One end of each of the wires 192 and 194 is connected to a separate end of each stimulator coil 174 and to the electrodes 184 and 186 as is illustrated in FIG. 9. The other ends of the wires 192 and 194 are connected to terminals 97a and 97b of the audio neutral circuit of FIG. 2, so that electrical signals characteristic of the sound waves incident at the microphones 12-18 are applied to the coils 174 and the electrode 184 and 186 of each finger stimulator 170. A pair of velcro straps 198 and 199 are formed in each finger stimulator, e.g. by embedding the same in the plastic covering 182, to enable the stimulators to be releasably fastened to a deaf person's fingers or thumbs as is illustrated in FIG. 7. For example, the hook portion may be carried by the strap 198 and the loop portion by the strap 199. The strap 198 may be conveniently looped over the wearer's finger and pressed against the strap 199 so that the flexible sheet 180 with its attached electrodes is pressed against a portion of the skin (containing tactile nerve endings or corpuscles) of the deaf person.

The electrical signals applies to the coils 174 cause the magnets 176 to vibrate with frequency components characteristic of those present in the incident sound waves. At the same time the electrical signals are applied across the electrodes 184 and 186 to impart electrical impulses (i.e. in the form of an electric field) to the tactile nerve endings which are subjected to the vibrations from the magnet 176. The simultaneous application of vibrations and electrical impulses to the same tactile nerve endings apparently enables the nerve endings to respond to and transmit signals to the brain which are characteristic of the incident sound waves thereby enabling the deaf person to more readily understand oral communications.

It should be noted that the nerve stimulators 170 (or 20) may be used to stimulate tactile nerve endings located in parts of the body other than the finger tips. The finger tips have the greatest density of tactile nerve endings and therefore will more readily respond to the simultaneous application of electrical impulses and vibrations than other parts of the body.

There has thus been described an audio-neural communication system and method which is capable of providing stimulation (characteristic of incident sound waves) to the tactile sensory nerves. The system is relatively inexpensive and surgery is optional.

The method and system is uncomplicated and effective. It will be apparent to those skilled in the art that various modifications are possible without departing from the scope and spirit of the present invention.

What is claimed is:

1. A method of communicating information representative of sound waves to a deaf person comprising the steps of:
    (a) translating the sound waves into electrical impulses and mechanical vibrations having characteristics representative of the sound waves;
    (b) applying the electrical impulses to tactile sensory nerves of the person; and
    (c) applying the mechanical vibrations to the same tactile sensory nerves whereby the electrical impulses enable the nerves to respond to vibrations having the frequency components contained in normal speech.

2. The method of claim 1 wherein the tactile sensory nerves originate in the hand of the person.

3. The method of claim 1 wherein the step of applying the electrical impulses comprises applying the electrical impulses across two spaced-apart electrodes in contact with the person's pacinian or meisner nerve corpuscles.

4. The method of claim 3 wherein the step of applying the mechanical vibrations comprises applying the mechanical vibrations directly to said pacinian or meisner nerve corpuscles whereby the electrical impulses modify the regeneration time of said corpuscles to allow the corpuscles to discriminate between the high and low frequency vibrations characteristic of normal speech.

5. The method of claim 3 wherein the applying step comprises applying the electrical impulses across two spaced-apart electrodes in contact with at least one finger of one hand of the person.

6. The method of claim 2 wherein the tactile sensory nerve is a portion of the radial nerve.

7. The method of communicating information representative of air pressure sound waves to a deaf person, comprising the steps of:
    (a) translating the sound waves into electrical impulses:
    (b) amplifying the electrical impulses;
    (c) applying the electrical impulses to the tips of a plurality of the deaf person's fingers;
    (d) transforming the amplified electrical signals into mechanical vibrations; and
    (e) applying the vibrations to said plurality of fingers.

* * * * *

UNITED STATES PATENT AND TRADEMARK OFFICE
CERTIFICATE OF CORRECTION

PATENT NO. : 4,813,419
DATED : March 21, 1989
INVENTOR(S) : Jeffrey D. McConnell It is certified that error appears in the above-identified patent and that said Letters Patent is hereby corrected as shown below:

Column 1, line 53, "receiver" should read --received--.

Column 7, line 42, "the" (second occurrence) should read --and--.

Column 8, line 18, "platic" should read --plastic--.

Column 8, line 28, "neutral" should read --neural--.

Signed and Sealed this

Twenty-first Day of November, 1989

Attest:

JEFFREY M. SAMUELS

Attesting Officer     Acting Commissioner of Patents and Trademarks